(12) United States Patent
Wang

(10) Patent No.: US 11,674,834 B2
(45) Date of Patent: Jun. 13, 2023

(54) MEASUREMENT OF FLUID FLOW VELOCITY WITH HIGH SPATIAL AND TEMPORAL RESOLUTION

(71) Applicant: University of South Carolina, Columbia, SC (US)

(72) Inventor: Guiren Wang, Irmo, SC (US)

(73) Assignee: University of South Carolina, Columbia, SC (US)

( * ) Notice: Subject to any disclaimer, the term of this patent is extended or adjusted under 35 U.S.C. 154(b) by 908 days.

(21) Appl. No.: 16/558,410

(22) Filed: Sep. 3, 2019

(65) Prior Publication Data

US 2020/0132528 A1 Apr. 30, 2020

Related U.S. Application Data

(60) Provisional application No. 62/753,214, filed on Oct. 31, 2018.

(51) Int. Cl.
| | | |
|---|---|---|
| *G01F 1/00* | (2022.01) | |
| *G01F 1/7086* | (2022.01) | |
| *G01F 1/661* | (2022.01) | |
| *G01F 1/20* | (2006.01) | |
| *A61B 5/0285* | (2006.01) | |
| *H01S 3/02* | (2006.01) | |
| *H01S 3/00* | (2006.01) | |
| *A61B 5/026* | (2006.01) | |

(52) U.S. Cl.
CPC .......... *G01F 1/7086* (2013.01); *A61B 5/0261* (2013.01); *A61B 5/0285* (2013.01); *G01F 1/206* (2013.01); *G01F 1/661* (2013.01); *H01S 3/005* (2013.01); *H01S 3/0007* (2013.01); *H01S 3/02* (2013.01)

(58) Field of Classification Search
None
See application file for complete search history.

(56) References Cited

U.S. PATENT DOCUMENTS

| | | | | |
|---|---|---|---|---|
| 5,153,665 A | * | 10/1992 | Weinstein | G01F 1/7086 |
| | | | | 356/28 |
| 2007/0206179 A1 | * | 9/2007 | Wang | G01F 1/712 |
| | | | | 356/28 |
| 2019/0120673 A1 | * | 4/2019 | Cooksey | G01F 1/704 |

FOREIGN PATENT DOCUMENTS

EP 3018454 A1 * 5/2016 ........... G01F 1/7086

* cited by examiner

*Primary Examiner* — Mark Hellner
(74) *Attorney, Agent, or Firm* — Burr & Forman LLP; Douglas L. Lineberry

(57) ABSTRACT

The present disclosure provides methods and systems for flight velocimetry employing at least one bleaching laser, at least one detection laser, at least one dichroic mirror, an objective, a detection system, and a nano stage to bleach a dye to form a bleached blot in a flow pathway.

8 Claims, 7 Drawing Sheets

(a)

(b)

(c)

MEASUREMENT OF FLUID FLOW VELOCITY WITH HIGH SPATIAL AND TEMPORAL RESOLUTION

This invention was made with government support under CBET0954977 and CBET1040227 awarded by the National Science Foundation. The government has certain rights in the invention.

BACKGROUND OF THE INVENTION

1) Field of the Invention

The present invention relates to methods and systems for successfully and accurately measuring the flow velocity, velocity fluctuation and velocity profile of flows of fluids with unprecedented spatial and temporal resolution.

2) Description of Related Art

In many interfacial flows, such as flows near a wall or inside electric double layers in micro/nanofluidics, blood flows in near the wall or microvessels and capillaries, interstitial flows, and flows in a porous medium, there is an increasing need for measurement of fluid velocity, velocity fluctuation, and velocity profile in the transverse direction with simultaneously ultrahigh spatial and temporal resolution. Measurement of flow velocity is one of the major efforts in fluid dynamics. For instance, the flows in porous media in shell oil or human tissues, where the porous size can be from a few micrometers down to tens of nanometers, is poorly understood. Further, whether a fluid flow has a slip or non-slip boundary condition over a solid surface has been heavily debated over the past two centuries, but a convincing conclusion is still lacking.

In the biomedical field, such as in physiology, pathology and pharmacology, measuring blood flow velocity profile in a blood vessel is required in order to know the flow induced shear stress, mechanotransduction, and transport phenomena in blood circulation. The blood flow velocity profile in microvessels has never been directly measured because there is a cell-free layer, or endothelial glycocalyx layer, on the endothelial cells, where there are no particles or blood cells to serve as a flow tracer.

The endothelial glycocalyx layer is not just a passive membrane or barrier between blood and tissues, but also actively involved in many functions, such as the control and regulation of vascular tone, fluid and solute transport, haemostasis and coagulation and inflammatory responses. Most of these functions depend critically on the flow velocity profile and the flow induced shear stress at the endothelial surface in the vascular lumen. The physical property of the blood flow can therefore influence many aspects of vascular function, diseases and drug delivery. Since blood flows affect shear stress, which in turn determines mechanotransduction behavior of the endothelial glycocalyx layer, measuring velocity cross the endothelial glycocalyx layer is highly desired, especially with sufficiently high spatial and temporal resolution. The current disclosure uses cancer metastasis as an example to explain the need for velocimetry, but this disclosure should not be considered limited to cancer metastasis only.

Malignant cancer accounts for approximately ninety percent (90%) of cancer patient deaths. Despite extensive research being done in this area, advancements have been limited, and knowledge of the process is still filled with gaps. While cancer research has thus far been largely focused on biological research, such as gene and protein alterations, some researchers, such as the developers of the current disclosure, are beginning to take a more biophysical approach.

Understanding the mechanism of metastasis, the spread of tumor cells to other parts of the body, plays a great potential role in early cancer detection and cancer therapy. Metastasis begins with the process of angiogenesis, in which tumors send out signals to nearby blood vessels, causing them to expand and grow toward the tumors. This allows for the provision of oxygen and nutrients for the tumors, but also opens up a way for tumor cells to enter the blood vessel, a process called intravasation. Once inside the blood vessel, the tumor cell can then travel to any part of the body, and exit through a process called extravasation, which can lead to malignant tumor growth. While the process of extravasation is crucial to greater understanding of metastasis, knowledge on the subject is currently very limited.

Extravasation is largely influenced by blood flow, more specifically, the presence of shear stress in blood flow. This is due to the fact that liquid flows at different velocities at different radial positions in a tube, described by Poiseuille's law, so the velocity gradient causes shear force on tumor cells traveling through a capillary. This shear force can have two possible effects on extravasation: it can either decrease the likelihood of the process from occurring, or it could increase the chances of occurrence.

In extravasation, tumor cells must adhere to the basement membrane of the blood vessels with sufficient time to extravasate. However, due to the hydrodynamic shear force, the tumor cells would get pushed forward with the flow of blood, preventing the tumor cells from being able to adhere for long enough to transmigration through the vessel wall, thus hindering the process. On the other hand, shear stress can cause the tumor cells to experience a tumbling motion, allowing for the ligands on the cells to adhere to the receptors on the basement membrane wall and deform, increasing the surface area in contact with the basement membrane, and therefore increasing the likelihood of the cell extravasating. As a result, shear stress could play one of two possible roles in the process of metastasis.

Despite the significance of being able to measure the shear stress in blood flow, there is currently no reliable method to measure velocity on such a small scale both in vitro and in vivo, for several reasons: available techniques have poor spatial resolution; there is a cell-free layer in blood vessels, where there are no particles or cells, which are often used as flow tracers; the capillaries in the body may have too small of an inner diameter, approximately 4-10 μm. Current methods of velocimetry primarily rely on particles as tracers, such as micro Particle Image Velocimetry (μPIV). These methods are limited in accuracy and temporal and spatial resolution and cannot measure the velocity profile of a fluid in a tube on such a small scale as is necessary both in vitro and in vivo.

Currently most velocimetries primarily rely on particles as tracers, such as micro Particle Image Velocimetry (μPIV) and blood cells. However, micro/nanoparticles respond much faster to an applied electric field than does the liquid inside the micro/nanochannels in electrokinetics. In fact, for many popular microflows, such as electrokinetics (EK) and near wall flow, magnetophoresis, acoustophoresis, photophoresis and thermophoresis, particles have different velocity from their surrounding fluids. Even though after proper correction and only focused on the measurement of mean velocity, the theoretical results can be two orders higher than experimental measurements. Because of the presence of the electric double layer, particles used as a tracer cannot achieve to the near wall region to measure the flow there. For the blood flows within the endothelial glycocalyx layer, there are also no particles and cells to trace the flow.

For $\mu PIV^2$ or nanoPIV the resolution so far achieved is on the similar order of slip length, and it is difficult to determine whether there is slip flow if the measured slip length is in the same order of the spatial resolution of the measuring technique. If the size of the resolution is even larger than the slip length, it is impossible to directly measure the slip length accurately. Although nanoPIV is available, interaction between particles and wall due to the electric double layer may hamper measurement. High spatial resolution (about 50 nm) method was presented using atomic force microscopy (AFM) but due to its intrusive nature and issue of access to the enclosed flow channels, it would be very difficult to use this technique wherein there is no opened sidewall. Further, almost all optics-based method suffer from diffraction.

On the other hand, there is another type of measuring technique, i.e. Molecular Tagging Velocimetry (MTV), including using photobleaching. Although most molecular tracer based velocimeters can use a neutral dye to measure average velocity, their temporal and spatial resolution are limited. Laser-induced fluorescence photobleaching anemometer (LIFPA) can have simultaneously high temporal and spatial resolution, but is also limited to the diffraction limit. Stimulated emission depletion (STED), which can bypass the diffraction limit in physics, was for the first time applied to the field of micro/nanofluidics to develop the so called STED-LIFPA and a spatial resolution of 70 nm has been achieved. It is reported that this is the only study that has been able to acquire three dimensional velocity profiles below the microscale with molecular tracers. However, although it is very powerful, the main drawback of this method is the need of light intensity calibration with flow velocity prior to the measurements, and the method cannot penetrate deep into blood flow, if single photon absorption is used.

The ideal method for calibration should be calibration free and use the same setup with LIFPA. One potential method that can measure the calibration and match LIFPA's setup is to use time of flight. Prior work has developed a periodic photobleaching method, which can only measure the bulk average flow by measuring the time of flight of a bleached blot in the flow. However, this method needs two lenses: one for bleaching the dye and the other for measuring the fluorescence signal. Given the limited space available, this method cannot directly measure the distance between the focused positions of the two laser beams. Therefore, a calibration step is required to determine the distance. Furthermore, for the same reason, this method can only measure bulk flow velocity, but cannot measure the velocity profile. In addition, for most experiments that use a microscope, it is almost impossible to add a second objective to keep the two focused points sufficiently close, which is required for velocity profile measurement to avoid molecular diffusion influence which will reduce signal and measuring accuracy.

Despite the significance of being able to measure the flow velocity in blood flow, there is currently no method to measure velocity on such a small scale as microvessel and capillary, and within the endothelial glycocalyx layer for both in vitro and in vivo, micro/nanofluidics and interfacial flows. For instance, a capillary in the body may have an inner diameter of about 4-10 μm. Current methods of velocimetry primarily rely on particles as tracers, such as micro Particle Image Velocimetry (μPIV). These methods are limited in accuracy and temporal and spatial resolution, however, and cannot measure the velocity profile of a fluid in a tube on such small scale as necessary in vitro and in vivo. Accordingly, it is an object of the present disclosure to provide a novel molecular tracer-based method to measure transient flow velocity, velocity profiles in blood flow including microcapillaries and nanocapillaries in vitro and in vivo, called Time of Flight, Multiphoton (MP)-Laser Induced Fluorescence Photobleaching Anemometry (LIFPA), i.e. MP-LIFPA or MP stimulated emission depletion (STED) LIFPA, i.e. MP-STED-LIFPA, which can achieve resolution of 10-100 nm.

BRIEF SUMMARY OF THE INVENTION

The above objectives are accomplished according to the present disclosure invention by providing in a first embodiment, a system for time of flight velocimetry (TFV). The system includes at least one bleaching laser that generates at least one bleaching laser beam to bleach a dye to form a bleached blot at an initial position in a flow pathway, at least one detection laser, wherein the detection laser generates at least one detection laser beam, at least one dichroic mirror that reflects both the bleaching laser beam and the detection laser beam, an objective that focuses the bleaching laser beam and the detection laser beam into two distinct focal points, a detection system, a pump for creating a fluid flow, a nano or micro position stage. Further, the system may include at least one mirror to reflect and direct the bleaching laser beam and detection laser beam as well as at least one mirror to control and adjust position of the focus point of the bleaching beam, at least one mirror to control and adjust position of the focus point of the detection beam to control and adjust the distance between the focus point of the bleaching laser and the focus point of the detection laser beam. Still further, the system may include a function generator to form either the bleaching laser beam or the detection laser beam as a pulsed beam. Again, the system may include a beam expander through which the detection laser beam passes. Still yet, the detection system may include at least one collection lens, at least one optical filter, at least one detection system pinhole, and at least one photodetector. Further, the system may include a camera.

In a further embodiment, a multiphoton laser induced fluorescence photobleaching anemometry system is provided. The system may include at least one femtosecond or picosecond laser, which generates an excitation laser beam, at least one beam expander, at least one objective, which focuses the excitation laser beam, at least one dichroic mirror, at least one detection system, at least one pump, at least one fluid pathway, and a dye solution that is contained in and flows along the fluid pathway after exposure to the excitation laser beam, wherein extent of photobleaching in the dye solution is directly proportional to an amount of time of exposure to the excitation laser beam. Further, the system may include at least one mirror. Still further, the detection system may include at least one collection lens, at least one optical filter, at least one pinhole, and at least one photodetector. Again yet, the system may comprise multiphoton nonlinear absorption that generates fluorescence from the dye solution.

In a still further embodiment, a multiphoton stimulated emission depletion laser induced fluorescence photobleaching anemometry system is provided. This system includes at least one laser to generate at least one excitation beam, at least on laser to generate at least one depletion beam, at least one laser beam to bleach a dye to form a bleached blot at an initial position in a flow pathway, two mirrors to control the distance between the focus point of the bleaching beam and the focus point of the detection laser beam, a beam expander, at least one dichroic mirror, a detection system, an objective, a stage to control relative position of at least two laser foci points, and a flow field. The system may also include a delay line to control phase between the at least one excitation beam and the at least one depletion beam. Still yet, the system may include at least one mirror to reflect the excitation beam and the depletion beam. Yet further the system may include the at least one laser generating the at least one depletion beam is a femtosecond or picosecond laser. Still yet, the system may include an optical fiber stretching system. Again yet, the at least one laser generating the at least one depletion laser beam may be a picosecond laser or has a pulse width of picoseconds. Still again, the detection system may include at least one collection lens, at least one optical filter, at least one pinhole, and at least one photodetector.

In a still yet further embodiment, a molecular tracer-based method to measure flow velocity, velocity fluctuation and velocity profiles is provided. The method may include using a pulse bleaching laser to bleach a dye solution to generate a bleached blot at a first position in a flow pathway, analyzing the fluid flow pathway with a detection beam, using a lens to focus a pulse laser beam and the detection beam to two small foci to increase spatial resolution, detecting when the bleached blot arrives at a detection position in the fluid flow pathway, and detecting a trough time that develops in a time series based on the flow pathway and arrival of the bleached blot. Still further, the extent of photobleaching in the dye solution in the trough is directly proportional to an amount of time of exposure to the pulse bleaching laser. Still further, the extent of photobleaching in the dye solution in the detection point is directly proportional to an amount of time of exposure to the detection laser.

BRIEF DESCRIPTION OF THE DRAWINGS

The construction designed to carry out the invention will hereinafter be described, together with other features thereof. The invention will be more readily understood from a reading of the following specification and by reference to the accompanying drawings forming a part thereof, wherein an example of the invention is shown and wherein.

Figure 1:
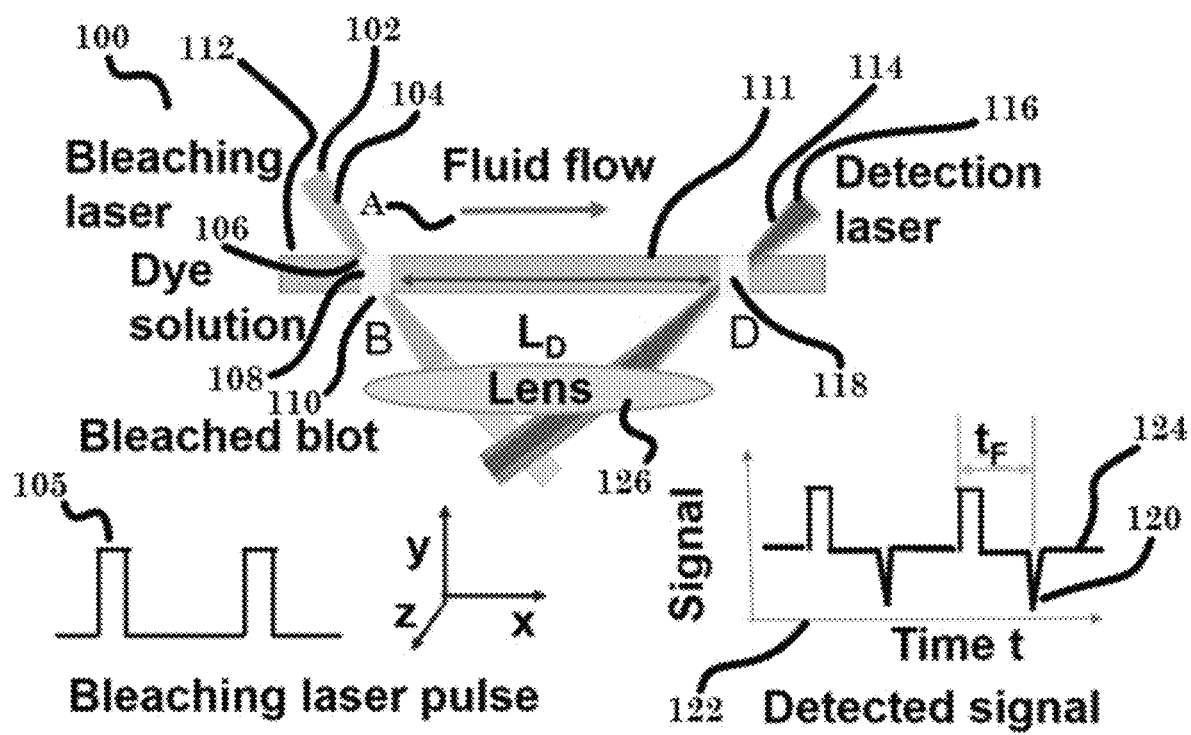
FIG. 1 shows the principle of TFV based on bleach and probe signal.

It will be understood by those skilled in the art that one or more aspects of this invention can meet certain objectives, while one or more other aspects can meet certain other objectives. Each objective may not apply equally, in all its respects, to every aspect of this invention. As such, the preceding objects can be viewed in the alternative with respect to any one aspect of this invention. These and other objects and features of the invention will become more fully apparent when the following detailed description is read in conjunction with the accompanying figures and examples. However, it is to be understood that both the foregoing summary of the invention and the following detailed description are of a preferred embodiment and not restrictive of the invention or other alternate embodiments of the invention. In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims. Likewise, other objects, features, benefits and advantages of the present invention will be apparent from this summary and certain embodiments described below, and will be readily apparent to those skilled in the art. Such objects, features, benefits and advantages will be apparent from the above in conjunction with the accompanying examples, data, figures and all reasonable inferences to be drawn therefrom, alone or with consideration of the references incorporated herein.

DETAILED DESCRIPTION OF A PREFERRED EMBODIMENT

With reference to the drawings, the invention will now be described in more detail. Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are herein described.

Unless specifically stated, terms and phrases used in this document, and variations thereof, unless otherwise expressly stated, should be construed as open ended as opposed to limiting. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise.

Furthermore, although items, elements or components of the disclosure may be described or claimed in the singular, the plural is contemplated to be within the scope thereof unless limitation to the singular is explicitly stated. The presence of broadening words and phrases such as "one or more," "at least," "but not limited to" or other like phrases in some instances shall not be read to mean that the narrower case is intended or required in instances where such broadening phrases may be absent.

The current disclosure provides a novel molecular tracer-based method to measure flow velocity, velocity fluctuation and velocity profiles. The present disclosure provides a single point photobleached time of flight velocimetry (TFV) that is calibration-free to measure flow velocity with just one objective. The TFV itself is a novel and calibration-free velocimetry. In TFV, two nonparallel focused light beams are used to measure the flow velocity.

Figure 2:
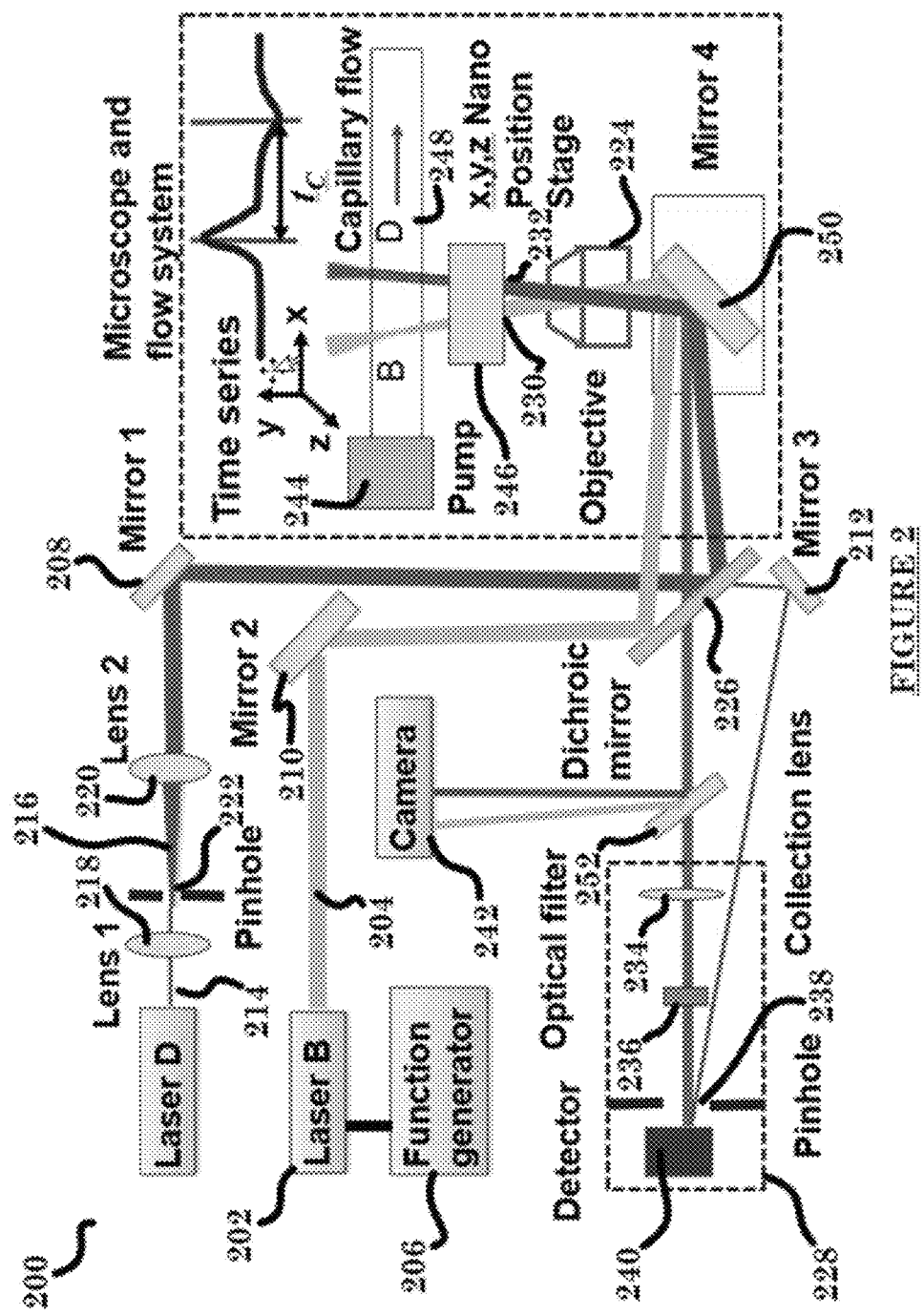
FIG. 2 shows one embodiment of a TFV system of the current disclosure.

The principle of the present TFV is in general based on bleach (or pumping a signal) and a probe signal as shown in FIG. 1, with the experimental setup shown in FIG. 2. For velocity measurement of one-dimensional flow (e.g., x-direction), the two points should be well aligned to have the same y and z position. When a pulsed laser with a given frequency is illuminated at an upstream point B, the dye there will be bleached. When fluorescence intensity is continuously measured at a downstream position D, there will be a trough in the signal when the bleached blot arrived at the detection point D after a peak due to the bleaching laser signal, which is also monitored by the same detector. Assuming the pulsed laser signal can also be measured continuously by the same detector, the convection time tc for the bleached blot to arrive to the point D can be measured from the time series of the fluorescence signal. The time tc is the time difference between the peak and trough. Then the flow velocity v can be determined as v=L/tc, where L is the distance between point B and D and can be directly measured with a camera and microscope stage micrometer as a calibration slide.

To determine the distance L between point B and D, a microscope stage micrometer will be placed at the focus point of the objective. L at the focused plane can be read by a camera using the imaging principle of an epifluorescence microscope. FIG. 2 shows an example, where a camera is located before the optical detector.

FIG. 1 shows one embodiment of a TFV design 100. A pulse bleaching laser 102 emitting a pulse laser beam 104, with a possible bleaching pulse pattern 105 shown enlarged, that bleaches a dye solution 106 to generate a bleached blot 108 at position B 110 in fluid flow pathway 111, the direction of fluid flow 112 is shown by arrow A. A detection beam 114 is generated by a detection laser 116 measures the arriving blot 108 at detection position D 118. There is a trough 120 in the time series 122 of the fluorescence signal 124 when bleached blot 108 passes through the detection laser 116 at position D 118. Lens 126 serves to focus pulse laser beam 104 and detection beam 114 to two small foci to increase spatial resolution.

To determine tc, one needs to know the start time of bleaching at point B in time series. For this goal, the pulsed laser light will also be led to the same detector through a beamsplitter (or dichroic) and a mirror as shown in FIG. 2. The peak in the time series is the starting time of the bleaching at B and the valley is the arrive time at point D. The difference between the arrive time and starting time is tc.

FIG. 2 shows an example setup for one embodiment of a TFV setup 200. Laser B 202 generates bleaching laser beam 204 used to bleach dye 106 to generate a bleached blot 108 at position B 110. Bleaching laser beam 204 can be controlled by function generator or laser chopper, to generate a pulsed laser, 206 to form laser beam 204 as a pulsed beam. Mirror 1 208, Mirror 2 210 and Mirror 3 212 are used to reflect and direct bleaching laser beam 204 and detection laser beam 214, while three mirrors are described, more or less mirrors are considered within the scope of this disclosure such as 1, 4, 5, 6, 7 or more mirrors. Of these, there may be at least one mirror to control and adjust position of the focus point of the bleaching beam, at least one mirror to control and adjust position of the focus point of the detection beam to control and adjust the distance between the focus point of the bleaching laser and the focus point of the detection laser beam. Detection laser beam 214 passes through beam expander 216, which may comprise Lens 1 218 and Lens 2 220 and pinhole 222, or in some embodiments, an optical fiber. Thus, the system may include at least one laser beam to bleach a dye to form a bleached blot at an initial position in a flow pathway, two mirrors to control the distance between the focus point of the bleaching beam and the focus point of the detection laser beam. Beam expander 216 is used to expand detection laser beam 214 to provide better focus. Both bleaching laser beam 204 and detection laser beam 214 are lead to objective 224 through a dichroic mirror 226, a mirror with significantly different reflection or transmission properties at different wavelengths. Dichroic mirror 226 reflects bleaching laser beam 204 and detection laser beam 214 and allows an emission fluorescence signal to transmit to detection system 228. Bleaching laser beam 204 and detection laser beam 214 are focused by objective 224 into two small foci 230 and 232 to increase spatial resolution. Detection system 228 may comprise collection lens 234 (to collect signal), optical filter (to filter away noise), detection system pinhole 238 (to increase spatial resolution) and photodetector 240 to measure the signal. Camera 242 is used to monitor the positions of the two beam foci 230 and 232. Pump 244 is used to deliver fluid for in vitro measurement and represents a heart for in vivo measurement. Nano position or micro position stage 246 is applied to control the relative spatial position between the foci 230 and 232 and flow field 248. Other elements such as Mirror 4 250, used to direct bleaching laser beam 204 and detection laser beam 214 to nano position stage 246 and camera dichroic mirror 252 allow the scattered bleaching laser beam and detection laser beam at foci 230 and 232 respectively to be reflected to the camera 242 to allow a full field of vision of the flow field 248 and foci 230 and 232.

There are several important issues that need to be addressed for high resolution measurement. First, only one objective may be used to obtain the two focus points having a distance L. To generate the two focused points with just one objective, two laser beams are required and should not be parallel, but with an angle which can be adjusted by tuning the angle of mirror 1 208 and mirror 2 210 respectively. The larger the angle, the larger the L, which also decreases with the increase of the magnification of the objective.

Second, due to molecular diffusion, the signal is decreased with the increase of tc. Therefore, L should be adjustable and decrease if v is low.

Third, to ensure calibration-free operation, the distance should be directly measured. To measure L, one can use a microscope stage calibration slide having a micrometer at the focus position of the objective. Camera 242 is used to monitor the two focus points on the micrometer as shown in FIG. 2. The typical time series signal of TFV is given as the time series, see FIG. 1.

The temporal resolution of periodic time of flight velocimetry (TFV) is determined by the laser pulse width, L the pulse period and even flow velocity, and therefore is relatively slow on the order of a millisecond. However, because TFV shares the same optical setup, LIFPA can then be used to achieve high temporal resolution after calibration with TFV if needed.

The higher the flow velocity, the longer the distance should be. However, if the flow velocity is low, the distance should be small to avoid low signal due to recovery because of diffusion. Such a distance can be manipulated by either the angle between the two laser beams or the magnification of the objective. The larger the magnification, the smaller the distance. This feature enables a large and dynamic range of the velocity measurement.

The method may also be used as a calibration method for Laser Induced Fluorescence Photobleaching Anemometry (LIFPA) based velocimetry. Their combination, i.e. TFV-LIFPA, can achieve simultaneously high spatial and temporal resolution. TFV is applicable to both single photon or multiphoton absorption to bleach fluorescence signal to generate the bleached blot and to detect the signal.

Figure 3:
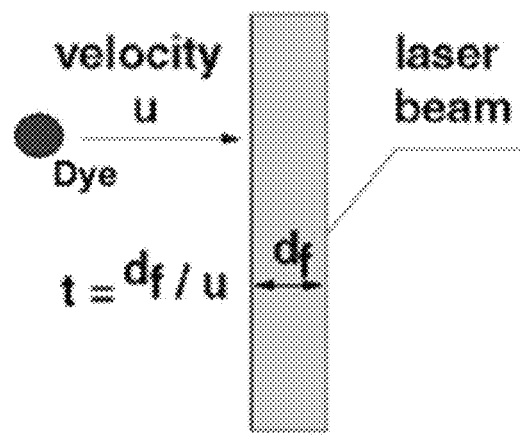
FIG. 3 shows principle of LIFPA and display at (a) dye molecules passed through a laser beam; (b) dynamic change of fluorescence intensity within the laser beam; and (c) Relation between average fluorescence intensity and flow velocity.
Figure 3:
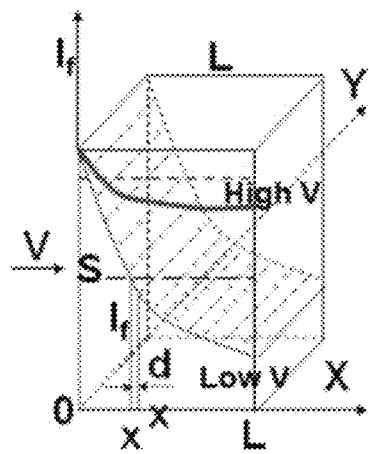
Figure 3:
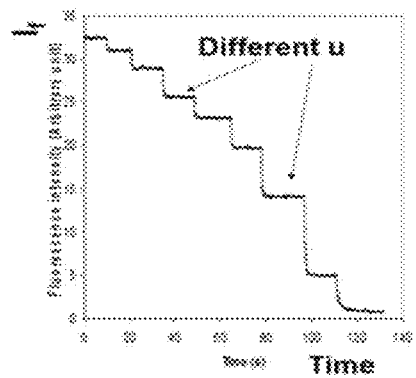

The principle behind LIFPA can be explained using the relationship between fluorescence intensity and fluid velocity for a given dye concentration, due to laser-induced fluorescence photobleaching as shown in FIG. 3. FIG. 3 shows the LIFPA principle: (a) the fluid with dissolved dye flows through a laser beam; (b) the dye solution flows through a laser beam at the focus point and the curves of high V and low V represent high flow velocity and low velocity, respectively; and (c) the fluorescence signal changes with flow velocity. The extent of photobleaching is directly proportional to the amount of time of exposure to light, so if there is no flow in the dye solution, the fluorescence intensity will decay with time, since the laser beam causes the dye within the light beam to photobleach. If the fluid flows more quickly, the average fluorescence will be greater since the fluid will be exposed to the laser beam for a less amount of time. Therefore, the higher the fluid velocity, the larger the average fluorescence intensity.

So far, LIFPA has only been applied to water solutions. This current method faces challenges when measuring the velocity profile of blood in vivo, and large blood vessel in vitro, as LIFPA is based on single-photon absorption for fluorescence and uses visible light. The visible light from the laser beam gets absorbed by the blood and the wall of blood vessels before it even reaches the detection point, so the light cannot penetrate the blood vessels and blood, preventing the application of LIFPA with visible light in vivo and large blood vessels in vitro.

To enable deep penetration for fluids with strong absorption of visible or UV light, such as blood flows in circulation system, the current disclosure uses multiphoton (e.g., two photon or three photon absorption but more or less photons are considered within the scope of this disclosure and hereby disclosed) absorption LIFPA or Mulit-photon-Laser Induced Fluorescence Photobleaching Anemometry (MP-LIFPA) which can achieve resolution of 100 nm. The flows can be, but are not limited to, flows in blood vessels, microvessels and capillaries both in vitro and in vivo or other interfacial flows or flows in microchannels and nanochannels. The disclosure provides a novel velocimetry to measure fluid (including, but limited to blood or other bodily fluids) flow velocity with high spatial and temporal resolution.

As a result, (MP)-LIFPA has been proposed, which uses a near infrared laser beam. This beam is able to penetrate through the wall of blood vessels and blood to reach deep tissue since it has a smaller absorption coefficient, allowing for accurate fluorescence measurement in vivo and in vitro and even in large blood vessels. However, infrared light itself does not allow for strong visible fluorescence, since the absorption of dye at the infrared beam's wavelength is very low, almost zero. To address this issue, multiphotons can be used instead. Single-photon absorption is commonly used as a linear process, where fluorescence intensity is linearly proportional to the laser power. However, MP absorption is a nonlinear process, in which the second photon generates enough energy to produce fluorescence that merely one photon cannot. For instance, if an 800 nm excitation beam is used in MP absorption, the effect is comparable to dye excited at 400 nm in single-photon absorption on when the laser power is sufficiently high This method could allow for much greater spatiotemporal resolution and practicality than current methods in medical diagnostics. In addition, MP-LIFPA will be applied not only to cancer research, but also to other fields, such as research on cardiovascular relevant diseases.

Figure 4:
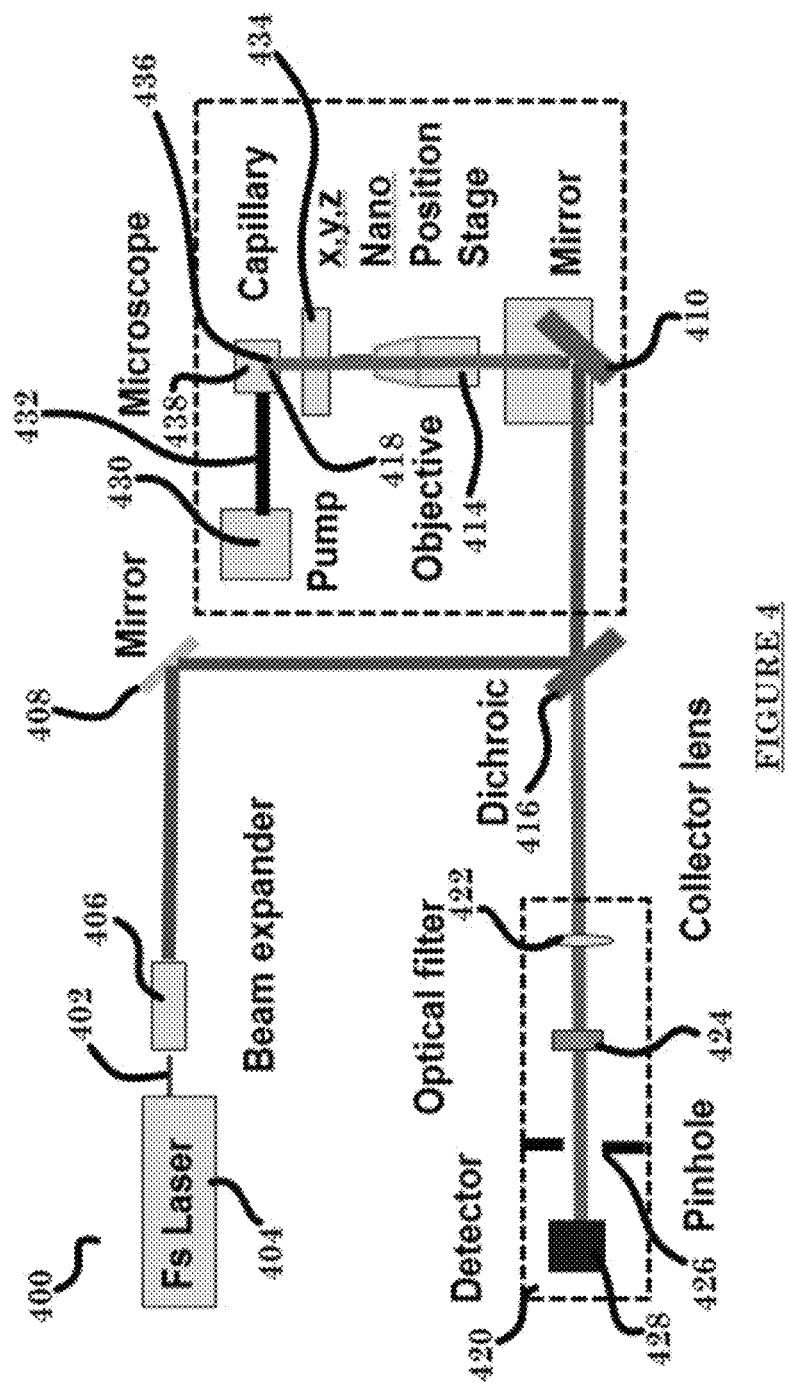
FIG. 4 shows one embodiment of a setup of a MP-LIFPA system of the current disclosure.

The experimental setup for MP-LIFPA is shown in FIG. 4. To begin the experiment, optic pieces are aligned to ensure the laser beam is focused correctly at the detection point on the microscope. A tunable picosecond or femtosecond pulse laser may be used as the excitation beam. The laser power is higher than a threshold value. While the average pulse laser power is not very high, each pulse has a very high power, which is sufficient for this technique. The blood vessel or flow channels will be mounted on a precise 3D nanostage on a stage.

FIG. 4 shows one embodiment of a set up and system for MP-LIFPA 400. Excitation laser beam 402, generated by a femtosecond or picosecond laser 404, has near IR wavelength and passes excitation laser beam 402 through MP-LIFPA beam expander 406, which is used to better focus excitation laser beam 402 to increase spatial resolution. All the mirrors, MP-LIFPA Mirrors 408 and 410 to reflect excitation laser beam 402. Excitation laser beam 402 is lead to objective 414 via a MP-LIFPA dichroic mirror 416. Excitation laser beam 402 is focused by objective 414 into a small focus point 418 to increase spatial resolution. Detection system 420 comprises a collection lens 422, at least one lens but more are considered within the scope of this disclosure and hereby so disclosed, to collect signals, MP-LIFPA optical filter 424 (to filter away noise), MP-LIFPA pinhole 426 (to increase spatial resolution) and photodetector 428 to measure the signal. MP-LIFPA Pump 430 is used to deliver fluid 432 for in vitro measurement and represents a heart for in vivo measurement. MP-LIFPA x, y, z nano position stage 434 is applied to control the relative spatial position between MP-LIFPA foci 436 and flow field 438.

A translation stage is needed to change the relative position between the detection position and the flow fields by moving either the flowing devices or laser beams. The stage resolution determines the positioning resolution of the system.

The laser beam is aligned to the microscope, and the objective can be used to focus the laser beam into the detection position of the flow field. To focus the beam to a smaller diameter, a beam expander is installed between the laser and microscope to expand the laser beam. The fluids can be pumped with a pump for in vitro measurement or blood flow for in vivo measurement, A photon detector is used to pick up fluorescence signals from the fluids flowing through the device. These signals will be recorded to a computer hard drive. A calibration curve (fluorescence v. velocity) should be found first, which can be obtained through other methods, such as TFV. Finally, all the data collected will be processed to obtain velocities at different radial positions of the flows by manipulating various positions and measuring the fluorescence signal at each position.

Figure 5:
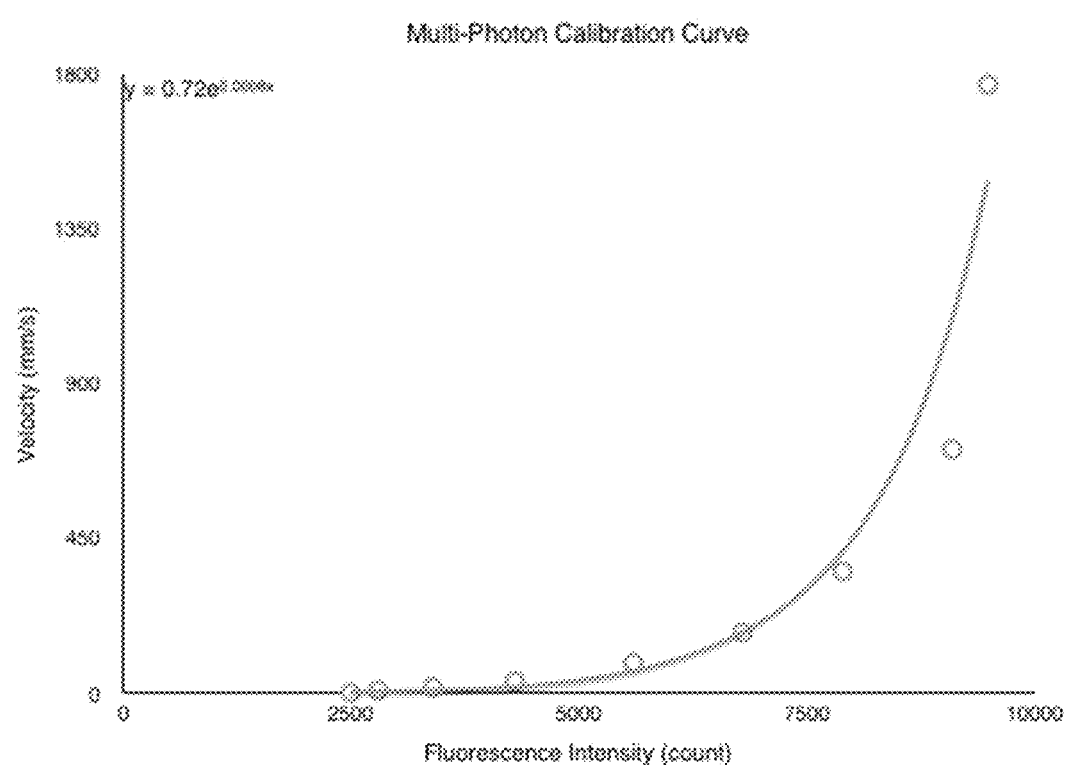
FIG. 5 shows a signal transduction and calibration curve which can be obtained by TFV.

The fluorescence intensity must be proportional to the velocity of the fluid. This relationship should be established as a calibration curve, which is shown in FIG. 5 as a typical one, where the fluorescence intensity does increase with the velocity. The calibration curve is then used to measure the velocity profile in the flows by measuring the fluorescence intensity at different positions. FIG. 5 shows an example of a typical relationship between fluorescence signal and flow velocity for MP-LIFPA.

Figure 6:
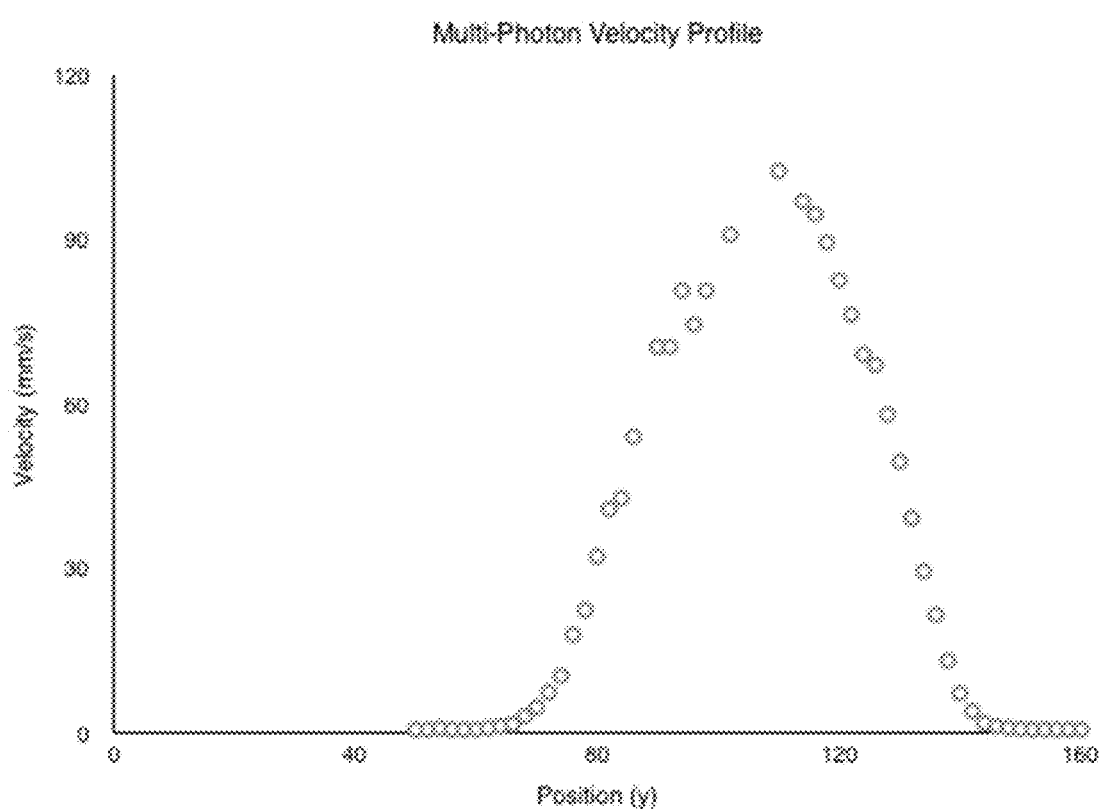
FIG. 6 shows a measured velocity provide with MP-LIFPA.

Based on the measurement from MP-LIFPA, FIG. 6 shows a measured symmetrical parabolic curve, much like one would expect to see of a fluid, such as water solution with fluorescent dye, passing through a capillary tube, demonstrating Poiseuille's law. Being able to measure the velocity profile of blood flows through microvessels will not only allow for greater understanding of the process of extravasation and how the specifics of blood flow affect it, but will also enable a more accurate and representative physiological environment for future in vitro research of blood flow, as well as optimize pharmacology of future cancer treatment drugs based on how they operate under different flow conditions. FIG. 6 shows an example of MP-LIFPA, similar results may be obtained with TFV. A similar result may also be obtained by TFV or MP-STED-LIFPA.

Figure 7:
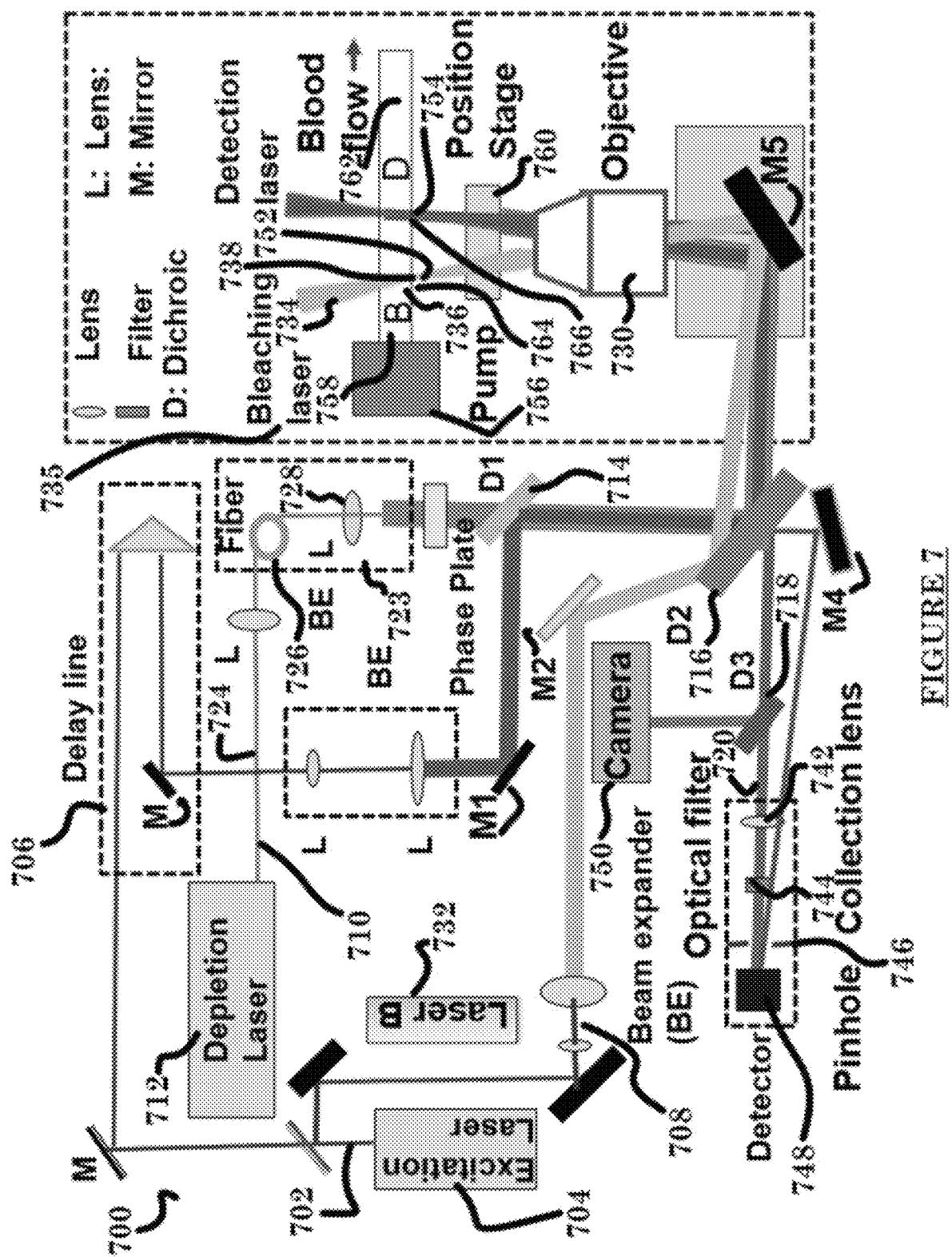
FIG. 7 shows a MP-STED-LIFPA system of the current disclosure.

When combined with two-photon and stimulated emission depletion (STED), we will have a MP-STED-LIFPA system and nanoscopic spatial resolution can be achieved with the resolution on the order of 10 nm. Such a system is shown in FIG. 7. In MP-STED-LIFPA, there is an excitation laser and a depletion laser beams. Both are pulsed. The pulse width of the depletion laser is better larger than 50 picoseconds and larger than that of the excitation beam. The depletion laser is modulated into a donut pattern through a phase plate. Both excitation and depletion laser beams should be temporally and spatially aligned. They are temporally aligned by a time delay line to be sufficiently close to get depletion effect and spatially aligned to be parallel and concentric and focused at the same point. The wavelength of the excitation is in the range of near infrared. Compared with single-photon based STED-LIFPA, MP-STED-LIFPA can have better spatial resolution, deeper penetration, less noise and less phototoxicity. Therefore, combining these together, the current disclosure provides a new velocimetry system with high spatial resolution and deep penetration. FIG. 7 is just an example to illustrate the current disclosure. The bleaching laser and detection lasers are interchangeable in FIG. 7, i.e. the STED system can be used for bleaching laser at point B as well.

FIG. 7 shows an example of one embodiment of a MP-STED-LIFPA system 700 of the current disclosure. MP-STED-LIFPA excitation beam 702, which may be generated by a femtosecond laser 704, has near IR wavelength, passes a delay line 706 and a MP-STED-LIFPA beam expander 708. Delay line 706 is used to control the phase between MP-STED-LIFPA excitation beam 702 and MP-STED-LIFPA depletion beam 710 and bleaching laser 735, generated by MP-STED-LIFPA depletion laser 712, to optimize the depletion effect. Beam expander 708 is used to expand MP-STED-LIFPA excitation beam 702, depletion beam 710, and bleaching beam 734 to improve focus. All mirrors, labeled M, M1, M2, M4, M5 are used to reflect MP-STED-LIFPA excitation beam 702 and MP-STED-LIFPA depletion beam 710 and bleaching laser 735. First Dichroic mirror 714 reflects MP-STED-LIFPA excitation beam 702 and allows MP-STED-LIFPA depletion laser 712 to transmit. Second Dichroic mirror 716 reflects MP-STED-LIFPA excitation beam 702 and allow emission fluorescence signal to transmit to the detector. Third dichroic mirror 718 reflects the scattered foci of the MP-STED-LIFPA excitation beam 702, MP-STED-LIFPA depletion beam 710, bleaching beam 734 to camera 750, and allows emission fluorescence signal 720 to transmit to the MP-STED-LIFPA detector 722. Depletion laser beam 712, in one embodiment, a femtosecond laser, is stretched by an optical fiber 724 stretching system 723, however this element may be omitted and stretcher 726 is not needed if the beam is generated from a picosecond laser, and expanded with a stretcher lens 728. Both MP-STED-LIFPA excitation beam 702 and MP-STED-LIFPA depletion beam 710 meet at first dichroic mirror 714 and are lead to MP-STED-LIFPA objective 730 through second dichroic mirror 716 and mirror M5 to objective 730. Laser B 732 generates the MP-STED-LIFPA bleaching beam 734 used to bleach the MP-STED-LIFPA dye 736 to generate a bleached blot at MP-STED-LIFPA position B 738. MP-STED-LIFPA bleaching beam 734 can also be obtained from MP-STED-LIFPA excitation laser 704 by adding a beam splitter, or by adding an additional laser such as Laser B 732. MP-STED-LIFPA detection system 740 may comprise a MP-STED-LIFPA collection lens 742, comprising at least one lens, to collect signals, MP-STED-LIFPA optical filter 744 to filter away noise, MP-STED-LIFPA pinhole 746 (to increase spatial resolution) and MP-STED-LIFPA photodetector 748 to measure the signal. Camera 750 is used to monitor the positions of the two MP-STED-LIFPA beam foci 752 and 754. MP-STED-LIFPA pump 756 is used to deliver MP-STED-LIFPA fluid 758 for in vitro measurement and represents a heart for in vivo measurement. Position stage 760 is applied to control the relative spatial position between MP-STED-LIFPA foci 764 and 766 and MP-STED-LIFPA flow field 762.

The current disclosure's method TFV shares the same optical setup with LIFPA and without the need of any change in a LIFPA based system and can therefore directly be applied for calibration LIFPA at any time if needed. The method is also compatible with MP-LIFPA or MP-STED-LIFPA for nanoscopic measurement.

For TFV, high repetition rate lasers, such as femtosecond or picosecond lasers, or combination of both, can be used for the bleaching and detection lasers. In this case, if the light wavelength is in near infrared range, we can have MP-TFV combination for higher spatial resolution measurement.

For TFV, the bleaching and detection beams can both be STED system, i.e. both have a parallel and concentric excitation and depletion (donut pattern) respectively. In this combination, we have STED-TFV system for higher spatial resolution measurement.

The current disclosure should not be considered limited to blood flow uses but should be considered applicable for flow of all fluids. It may also be used for near wall flow velocity measurement in water and other fluids. The current disclosure may also be used not only for in vivo, but also ex vivo, in vitro and for general fluid flow velocity as well.

The current disclosure provides three modalities for velocity measurement: TFV, multiphoton (e.g. at least two photons) LIFPA and multiphoton-STED-LIFPA. TFV can also combined with MP and STED to have MP-TFV and STED-TFV respectively. TFV can be used for both calibration for LIFPA application and velocimetry. Further, the disclosure should not be considered limited to multiphoton applications as it can be used for single photon absorption as well, i.e., it can use continuous wave lasers. The current method covers using molecular dyes as a tracer and photobleaching for signal transduction. TFV can also be used for calibration for MP-LIFPA and MP-STED-LIFPA for blood flows and for high resolution.

While the present subject matter has been described in detail with respect to specific exemplary embodiments and methods thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art using the teachings disclosed herein.

What is claimed is:

1. A system for time of flight velocimetry comprising:
at least one bleaching laser, wherein the bleaching laser generates at least one bleaching laser beam to bleach a dye to form a bleached blot at an initial position in a flow pathway;
at least one detection laser, wherein the detection laser generates at least one detection laser beam;
at least one dichroic mirror that reflects both the bleaching laser beam and the detection laser beam;
an objective that focuses the bleaching laser beam and the detection laser beam into two distinct focal points;
a detection system; and
a nano or micro position stage.

2. The system of claim 1, further comprising at least one mirror to reflect and direct the bleaching laser beam and detection laser beam.

3. The system of claim 1, further comprising a function generator to form either the bleaching laser beam or the detection laser beam as a pulsed beam.

4. The system of claim 1, further comprising a beam expander through which the detection laser beam passes.

5. The system of claim 1, wherein the detection system comprises at least one collection lens, at least one optical filter, at least one detection system pinhole, and at least one photodetector.

6. The system of claim 1, further comprising a camera.

7. A molecular tracer-based method to measure flow velocity, velocity fluctuation and velocity profiles comprising:
using a pulse bleaching laser to bleach a dye solution to generate a bleached blot at a first position in a flow pathway;
analyzing the fluid flow pathway with a detection beam;
using a lens to focus a pulse laser beam and the detection beam to two small foci to increase spatial resolution
detecting when the bleached blot arrives at a detection position in the fluid flow pathway; and
detecting time difference between the peak and a trough time that develops in a time series based on the flow pathway and starting of bleaching to generate the bleached blot and arrival of the bleached blot.

8. The method of claim 7, wherein extent of photobleaching in the dye solution is directly proportional to an amount of time of exposure to the pulse bleaching laser.

* * * * *